US00PP37663P2

(12) United States Plant Patent
Suiker

(10) Patent No.: US PP37,663 P2
(45) Date of Patent: Sep. 1, 2026

(54) STRAWBERRY PLANT NAMED 'Ferosa'

(50) Latin Name: ***Fragaria* x *ananassa***
Varietal Denomination: Ferosa

(71) Applicant: Flevo Berry Holding B.V., Ens (NL)

(72) Inventor: Marcel Suiker, Ens (NL)

(73) Assignee: Flevo Berry Holding B.V., Ens (NL)

( * ) Notice: Subject to any disclaimer, the term of this patent is extended or adjusted under 35 U.S.C. 154(b) by 0 days.

(21) Appl. No.: 19/462,915

(22) Filed: Jan. 28, 2026

(30) Foreign Application Priority Data

Jul. 31, 2025 (QZ) ..... PBR 2025/1709

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./208, 209
See application file for complete search history.

*Primary Examiner* — Susan Mccormick Ewoldt
(74) *Attorney, Agent, or Firm* — James R. Holm; Plant Novelty Rights, LLC

(57) ABSTRACT

A new and distinct strawberry plant named 'Ferosa' particularly distinguished by a smooth, bright and glossy fruit surface with evenly distributed achenes, uniformly conical fruit shape, a compact, uniform and spreading growth habit with inflorescence positioned above the foliage, and a low number of flowers per inflorescence and reduced stolon prominence.

4 Drawing Sheets

Figure 1:
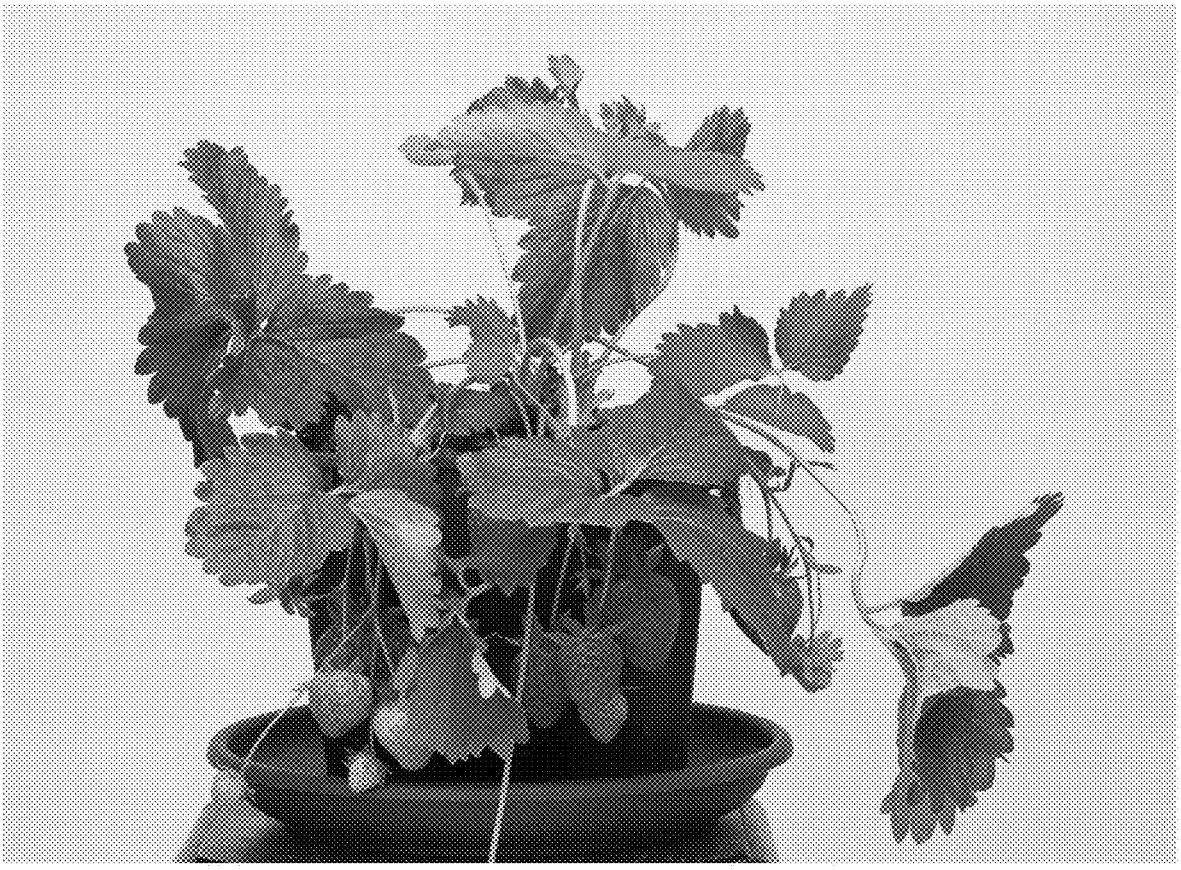

Genus and species: *Fragaria* x *ananassa*.
Variety denomination: 'Ferosa'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the filing date. This application claims priority to CPVO application No. 2025/1709 filed on Jul. 31, 2025, which is herein incorporated by reference.

BACKGROUND OF THE NEW PLANT

The present invention comprises a new and distinct variety of strawberry plant, botanically known as *Fragaria* x *ananassa*, and hereinafter referred to by the variety name 'Ferosa'. The new strawberry variety 'Ferosa' is a seedling selection that resulted from a controlled pollination breeding program carried out in April of 2019 in Ens, Netherlands. The new variety originated as a seedling from crossing the proprietary strawberry breeding line '13-115' (unpatented), as the seed parent, with the proprietary strawberry breeding line '11-87' (unpatented) as the pollen parent. Seed from said cross was harvested, then germinated, and the resulting seedlings were grown to a mature size in order to evaluate for desirable commercial characteristics. In August of 2020, the inventor selected the claimed strawberry variety from amongst said seedlings for further evaluation to determine its distinctness and stability of the unique characteristics first observed.

Asexual reproduction of 'Ferosa', by way of vegetative cuttings, was first performed in September of 2020 in Ens, Netherlands. Through five subsequent generations of asexual propagation, the unique features of this new strawberry variety 'Ferosa' have proven to be stable and remain true to type.

SUMMARY OF THE INVENTION

The new strawberry variety 'Ferosa' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new strawberry variety. The combination of these characteristics distinguishes 'Ferosa' as a new and distinct variety of strawberry.

1. Strawberry 'Ferosa' exhibits a smooth, bright and glossy fruit surface with evenly distributed achenes;
2. Strawberry 'Ferosa' exhibits uniformly conical fruit shape;
3. Strawberry 'Ferosa' exhibits a compact, uniform and spreading growth habit with inflorescence positioned above the foliage; and
4. Strawberry 'Ferosa' exhibits a low number of flowers per inflorescence and reduced stolon prominence.

DESCRIPTION OF THE PHOTOGRAPHS

This new strawberry variety is illustrated by the accompanying-colored photographs which show the overall appearance and distinct characteristics of the plant.

The colors shown are as true as can be reasonably obtained by conventional photographic procedures.

The photographs are of 12-month-old plants grown in 19-centimeter square containers in a conventional cold-story glasshouse in Ens, Netherlands.

Colors in the photographs may differ slightly from the color values cited in the botanical description which accurately describes the colors of the new variety.

FIG. 1. shows the overall plant form, foliage, and fruit of 'Ferosa'.

Figure 2:
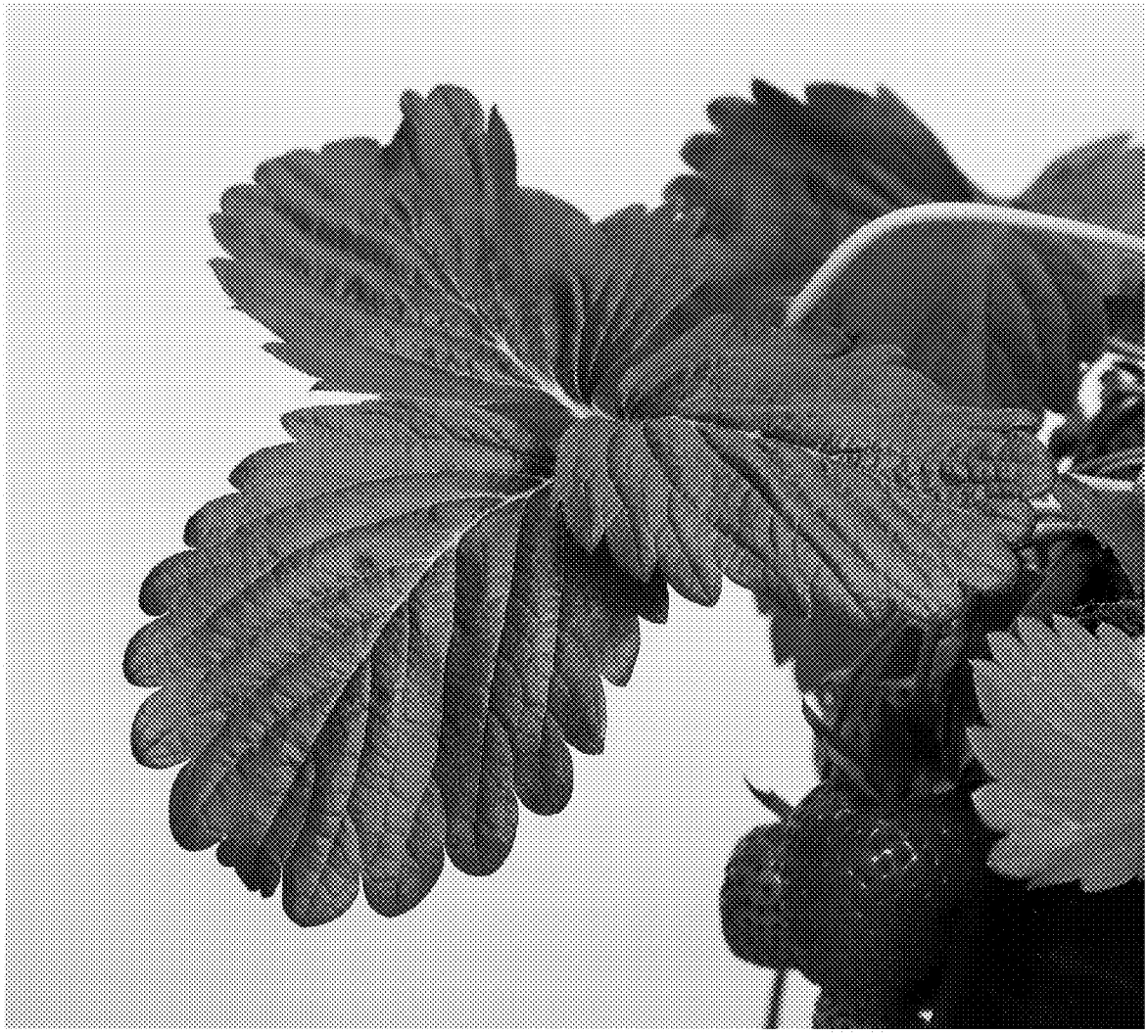

FIG. 2. shows a close-up of a typical leaf observed on plants of 'Ferosa'.

Figure 3:
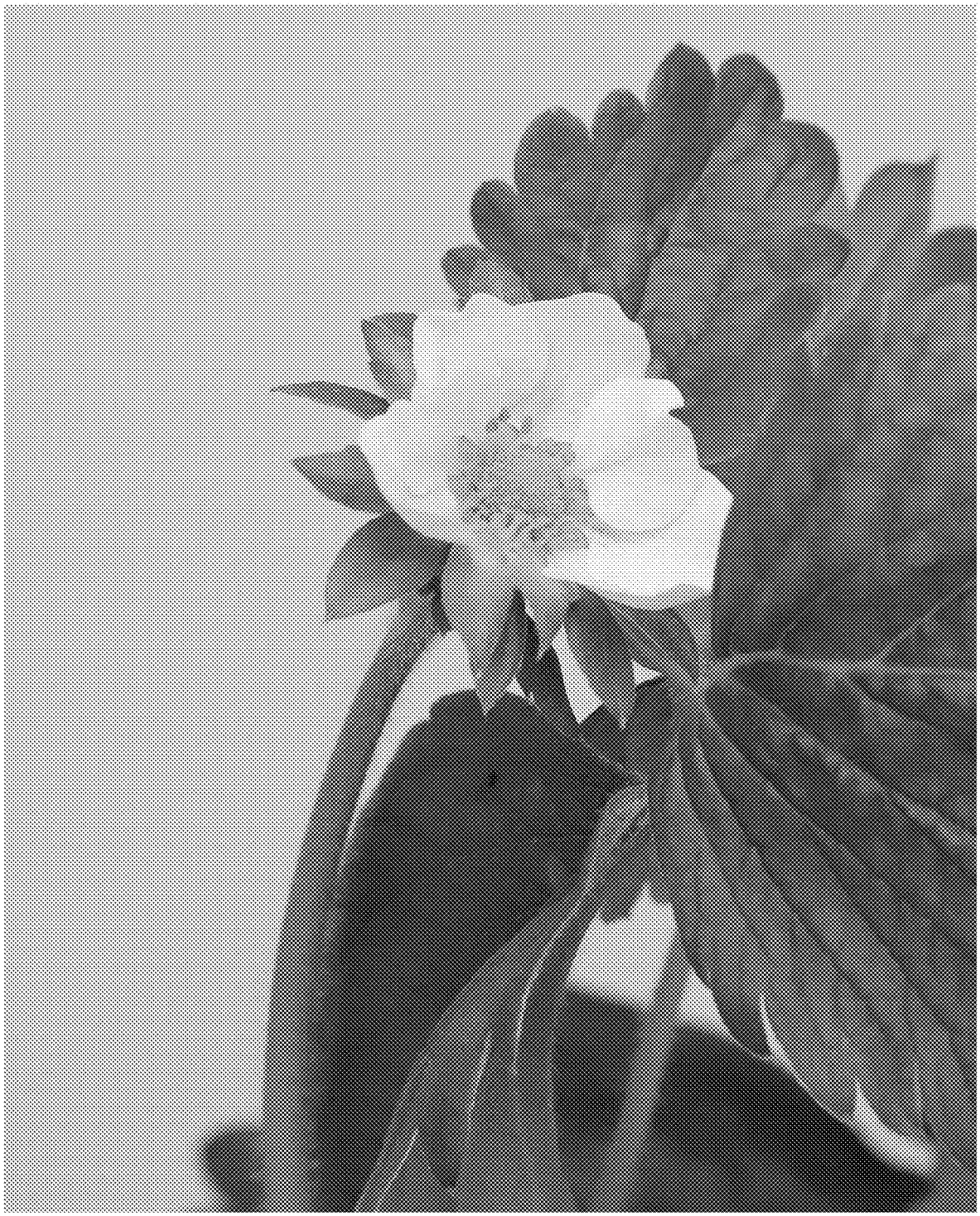

FIG. 3. shows a close-up of a typical flower observed on plants of 'Ferosa'.

Figure 4:
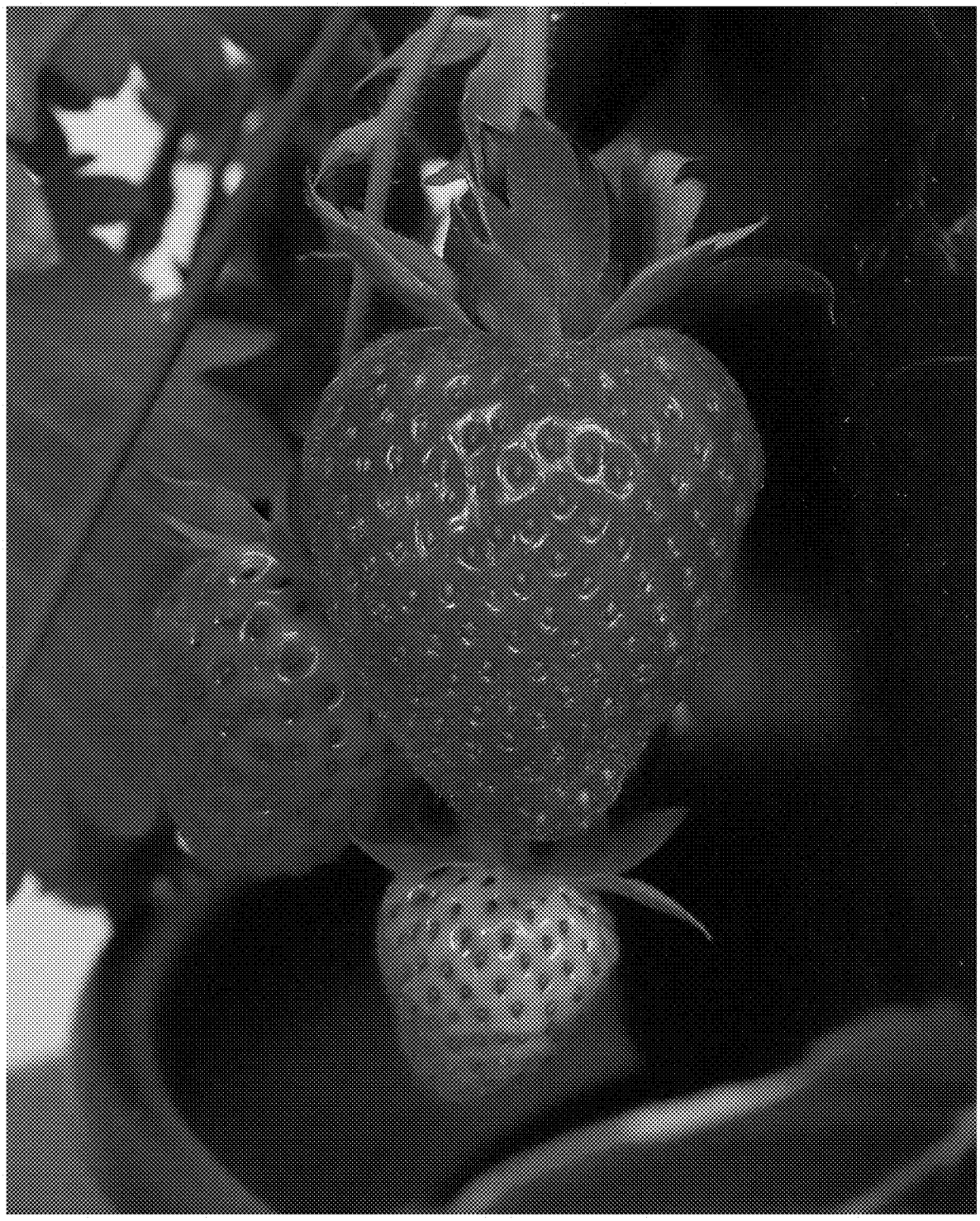

FIG. 4. shows typical fruit observed on plants of 'Ferosa'.

DESCRIPTION OF THE NEW VARIETY

The following is a detailed botanical description of the new and distinct variety of strawberry known as 'Ferosa', based upon observations of 12-month-old plants grown in 19-centimeter square containers in a conventional cold greenhouse located in Ens, Netherlands. Plants were grown on benches in a non-climate-controlled greenhouse, using conventional production protocols for strawberry plants which consisted of drip irrigation with fertigation applications as needed. Biological insect control measures were utilized in production. Plants were produced with full sun exposure and no photoperiodic treatments or artificial light was given to the plants. Temperatures ranged from 18 to 30 degrees Celsius during the day and 5 to 18 degrees Celsius at night. Observation data was recorded in September of 2025. Those skilled in the art will appreciate that certain characteristics will vary with older or, conversely, with younger plants. 'Ferosa' has not been observed under all possible environmental conditions. Where dimensions, sizes, colors and other characteristics are given, it is to be understood that such characteristics are approximations or averages set forth as accurately as practicable. The phenotype of the new variety may differ from the descriptions set forth herein with variations in environmental, climatic and cultural conditions. In the following description, color references are made to The Royal Horticultural Society Colour Chart, Sixth Edition 2019 reprint, except where general color terms of ordinary dictionary significance are used.

DETAILED BOTANICAL DESCRIPTION

Classification:

*Family.*—Rosaceae.

*Botanical.*—*Fragaria* x *ananassa.*

*Denomination.*—'Ferosa'.

*Common name.*—Strawberry.

Plant description:

*General.*—Acaulescent, stoloniferous herbaceous perennial with leaves and inflorescence developing from basal rosettes with approximately 3 rosettes per plant; no lateral branching is present.

*Growth habit.*—Compact, uniform and spreading.

*Overall plant shape.*—Flattened with pendulous stolons.

*Average height*—20.7 cm to the top of the foliar plane; 19.6 cm to the top of the floral plane.

*Average width.*—44.8 cm.

*Plant vigor.*—Moderate.

*Growth rate.*—Moderate.

Stolon description:

*Appearance and shape.*—Pendulous (or creeping when not grown in a hanging basket); circular in cross section.

*Aspect* (*angle from vertical*).—Average 70 degrees but curled downward to vertical.

*Length.*—55.0 cm.

*Diameter.*—0.3 cm.

*Internode length.*—27.5 cm.

*Strength.*—Strong.

*Texture.*—Sparsely to moderately covered with very thin, short hairs with an average length of 0.1 cm; hairs are colored a transparent white but too sparsely present to measure R.H.S. color designation.

*Luster.*—Matte.

*Color.*—Immature stolons: Near 144B (yellow-green). Mature stolons: Near 144A (yellow-green). At internodes: Near 144A (yellow-green).

Foliage description:

*Arrangement.*—Alternate in basal rosettes.

*Attachment.*—Petiolate.

*Division.*—Trifoliate.

*Compound leaf outline.*—Reniform.

*Length.*—15.3 cm, excluding the petiole.

*Width.*—18.7 cm.

*Quantity.*—6 leaves per rosette.

*Leaflets.*—Quantity: 3. Shape: Varying from broad obovate to broad ovate, occasionally near orbicular. Length: 9.8 cm. Width: 8.9 cm. Aspect: Slightly concave. Apex: Minutely abruptly acute. Base: Broad attenuate to near obtuse. Margin: Coarsely dentate to crenate. Texture: Adaxial surface: Smooth except for the main vein and secondary veins which are very sparsely covered with very thin, soft hairs with an average length of 0.1 cm; hairs are colored a transparent white but too small and too sparsely present to measure R.H.S. color designation. Abaxial surface: Smooth except for the main vein and secondary veins which are moderately covered with very thin, soft adpressed hairs with an average length of 0.1 cm; hairs are colored a transparent white but too sparsely present to measure R.H.S. color designation. Rugosity (adaxial and abaxial surfaces): Slightly rugose. Luster: Adaxial surface: Slightly glossy. Abaxial surface: Matte. Color: Juvenile foliage: Adaxial surface: Near 143A and 143B (green). Abaxial surface: Near 138B (green). Mature foliage: Adaxial surface: Near 137A (green). Abaxial surface: 138B (green). Venation: Type: Pinnate. Color (mature leaf): Adaxial surface: Near N144A (yellow-green). Abaxial surface: Near 145C (yellow-green).

*Petiole.*—Length: 19.1 cm. Diameter: 0.3 cm, horizontal and vertical; petioles flattened on the adaxial surface. Strength: Strong. Texture: Sparsely to moderately covered with very thin, soft hairs with an average length of 0.1 cm; hairs are colored a transparent white but too small and too sparsely present to measure R.H.S. color designation. Luster (adaxial and abaxial surfaces): Slightly glossy. Color: Adaxial surface: Near 144C (yellow-green). Abaxial surface: Near 144B (yellow-green).

*Stipules.*—General: Two leafy stipules present at the base of each leaf. Shape: Lanceolate. Length: 2.8 cm. Width: 0.5 cm. Apex: Narrow acute. Base: Broad cuneate. Color (adaxial and abaxial surfaces): Near 145A to 145B (yellow-green). Texture: Adaxial surface: Glabrous. Abaxial surface: Covered with very thin, soft hairs with an average length of 0.1 cm; hairs are colored a transparent white but too small and too sparsely present to measure R.H.S. color designation.

Inflorescence description:

*Type.*—Compound cymose panicle.

*Natural flowering season.*—From spring into summer in Ens, Netherlands.

*Time to flower.*—9 months.

*Height.*—6.6 cm, excluding the peduncle.

*Diameter.*—6.9 cm.

*Quantity of flowers per inflorescence.*—Approximately 4.

*Quantity of flower buds per plant.*—Approximately 9.

*Quantity of flowers per plant.*—Approximately 20.

*Quantity of flowers and flower buds per plant.*—Approximately 20.

*Peduncle.*—Length: 13.2 cm. Diameter: 0.3 cm. Aspect: Average of 50 degrees to horizontal. Strength: Moderate to strong. Texture: Densely covered with thin, soft hairs with an average length of 0.1 cm; hairs are colored a transparent near NN155D (white). Luster: Slightly glossy. Color: Near 144B and 144C (yellow-green).

Flower buds:

*Shape.*—Ovate.

*Length.*—1.2 cm.

*Diameter.*—1.3 cm.

*Texture.*—Smooth and glabrous except for the immature sepals which are moderately covered with very thin, soft hairs with an average length of 0.5 mm; hairs are colored a transparent white but too small and too sparsely present to measure R.H.S. color designation.

*Luster.*—Matte.

*Color.*—Near 137B (green) and fading at the base to near 150A (yellow-green).

Flower:

*Form.*—Rotate; single.

*Aspect.*—Outwardly to upright.

*Habit.*—Low to moderate.

*Vertical height.*—3.0 cm.

*Horizontal diameter.*—3.0 cm.

*Depth:* 1.8 cm.

*Fragrance.*—Faintly sweet.

*Lastingness.*—Approximately 7 days.

*Persistence.*—Self-cleaning.

*Pedicels.*—Length: 2.3 cm. Diameter: 0.2 cm. Aspect: Approximately 30 degrees to the peduncle axis. Strength: Moderate. Texture: Densely covered with thin, soft hairs with an average length of 0.1 cm; hairs are colored a transparent near NN155D (white). Luster: Slightly glossy. Color: Near 144B (yellow-green).

*Petals.*—Arrangement: Rotate with a single whorl of free petals. Quantity: Average 8. Shape: Near orbicular and very slightly concave. Length: 1.4 cm. Width: 1.4 cm. Apex: Obtuse. Base: Broad cuneate. Margin: Entire, moderately undulated. Texture (adaxial and abaxial surfaces): Glabrous, smooth and moderately velvety. Rugosity: Non-rugose. Luster (adaxial and abaxial surfaces): Matte. Color when opening: Adaxial surface: NN155C (white) and fading at the base to near NN155A (white). Abaxial surface: 155C (white) and fading at the base to near NN155C (white). Color when fully opened: Adaxial surface: NN155C (white) and fading at the base to near NN155A (white). Abaxial surface: A blend of near 155C and NN155C (white) and fading at the base to near NN155A (white). Color when fading (adaxial and abaxial surfaces): Petals do not fade with age. Venation color when fully opened (adaxial and abaxial surfaces): Not visible.

*Calyx.*—Shape: Rotate. Length: 0.8 cm. Diameter: 3.7 cm. Sepals: Arrangement: Rotate with sepals in a single whorl and fused at the base. Quantity: Average 16.Length: 1.4 cm. Width: 0.5 cm. Shape: Obovate. Apex: Acute. Base: Cuneate. Margin: Entire, occasionally with a single tooth present on one side and sometimes both sides. Texture: Adaxial surface: Smooth, sparsely covered with very thin, soft hairs with an average length of 0.1 cm; hairs are colored a transparent white but too small and too sparsely present to measure R.H.S. color designation. Abaxial surface: Smooth, sparsely covered with very thin, soft hairs with an average length of 0.1 cm; hairs are colored a transparent white, but too small and too sparsely present to accurately measure R.H.S. color designation. Luster (adaxial and abaxial surfaces): Matte. Color when opening: Adaxial surface: Near 143A (green). Abaxial surface: Near 137B (green). Color when fully opened: Adaxial surface: Near 141A (green). Abaxial surface: Near 138B (green). Sepal spurs: Not present.

*Bracts.*—Position: Two bracts are present at the base of each pedicel. Shape: Narrow elliptic to narrow ovate. Length: 3.6 cm. Width: 2.6 cm. Apex: Acute. Base: Attenuate. Margins: Serrate to dentate-serrate. Color: Adaxial surface: 143A (green). Abaxial surface: Near 138B (green). Texture: Adaxial surface: Sparsely covered with thin, soft hairs with an average length of 0.5 mm; hairs are colored a transparent white but too small and too sparsely present to measure R.H.S. color designation. Abaxial surface: Moderately covered with thin, soft hairs with an average length of 0.1 cm; hairs are colored a transparent white but too small and too sparsely present to measure R.H.S. color designation.

Reproductive organs:

*Stamens.*—Quantity per flower: Average 32. Anthers: Shape: Oblong. Length: 0.75 mm. Width: 0.5 mm. Color: 22A (yellow-orange). Filaments: Length: 0.2 cm. Color: Near 145C (yellow-green). Pollen: Abundance: Low. Color: Near 13B to 13C (yellow).

*Pistil.*—Quantity per flower: 300. Length: 0.1 cm. Style: Length: 0.7 mm. Color: Near 150B (yellow-green). Stigma: Shape: Club-shaped. Length: 0.3 mm. Diameter: 0.3 mm. Color: Near 151D (yellow-green).

*Ovary color.*—Near 145B (yellow-green).

Seed and Fruit:

*Fruit.*—Harvest season: May through September in the Netherlands. Time to maturity: Approximately 5 weeks after flowering. Quantity per plant: 10.Dimensions: 4.9 cm long and 4.4 cm in diameter. Weight: Average 18.2 grams. Shape: Conical. Texture: Smooth and sparsely covered with very short, soft hairs with an average length of 0.4 mm; hairs are colored white but too small and too sparsely present to measure R.H.S. color designation. Luster: Glossy. Color (mature fruit): A blend of near 53A (red) and 185A (greyed- purple), closest to 185A. Fruit flavor: Slightly sweet and moderately acidic. Firmness of flesh: Soft. Lastingness of fruit: Approximately 1 week. Market use: Fresh fruit market.

*Achenes.*—Position: Below surface. Quantity per fruit: 200. Length: 0.125 cm. Diameter 0.08 cm. Texture: Smooth and glabrous. Color: A blend of near 183B and 187B (greyed-purple).

Environmental tolerances: Adapted to USDA Zones 4 through 9 and temperatures ranging from at least minus 32 degrees Celsius to 40 degrees Celsius; low to moderate tolerance to rain; moderate to high tolerance to wind.

Disease and pest tolerance: No claims are made to any superior disease or insect resistance or tolerance.

COMPARISON WITH THE PARENT PLANTS

The new strawberry variety 'Ferosa' can be distinguished from its seed parent '13-115' (unpatented) in the following characteristics described in Table 1 below.

TABLE 1

| Characteristic | 'Ferosa' | '13-115' |
|---|---|---|
| Plant habit. | More compact and uniform with foliage held close to the crown. | More spreading with looser overall structure. |
| Stolon formation. | Less prominent and shorter. | Stolons long and clearly trailing. |
| Fruit position. | Held closer to the crown and partially supported by the foliage. | Fruit hangs lower on longer peduncles. |
| Fruit shape. | Uniformly conical with well-defined apex. | Short conical to more rounded in shape. |
| Fruit surface appearance. | Smooth and glossy with evenly distributed achenes. | Less glossy with irregular achene distribution. |

The new strawberry variety 'Ferosa' can be distinguished from its pollen parent '11-87' (unpatented) in the following characteristics described in Table 2 below.

TABLE 2

| Characteristic | 'Ferosa' | '11-87' |
|---|---|---|
| Plant habit. | More compact and uniform with foliage held close to the crown. | More spreading, elongated and trailing. |
| Stolon formation. | Less prominent and shorter. | Long, thin and highly trailing. |
| Leaf arrangement. | Leaves held closer together forming a dense canopy. | More widely spaced and outwardly spreading. |
| Fruit position. | Held closer to the crown and partially supported by the foliage. | Borne on long peduncles and hanging well below the container |
| Fruit shape. | Uniformly conical with well-defined apex. | Variable, including short conical to irregular shapes. |

COMPARISON WITH RELATED KNOWN VARIETY

The new strawberry variety 'Ferosa' can be distinguished from the related known variety of strawberry plant 'Florice' (U.S. Plant Pat. No. 34,684) in the following characteristics described in Table 3 below.

TABLE 3

| Characteristic | 'Ferosa' | 'Florice' |
|---|---|---|
| Plant habit. | More compact and uniform with fruit held closer to the container. | More spreading with longer, trailing growth. |
| Stolon formation. | Less prominent and shorter. | Stolons long and clearly trailing. |
| Fruit shape. | Uniformly conical with well-defined apex. | Short conical, broader, and less uniform in shape. |
| Mature fruit external color. | Bright, glossy red. | Red, less glossy. |
| Fruit surface appearance. | Smooth and glossy with evenly distributed achenes. | Slightly uneven surface with irregular achene distribution. |

What is claimed is:

1. A new and distinct variety of strawberry plant named 'Ferosa', substantially as illustrated and described herein.

* * * * *